(12) United States Patent
Luo

(10) Patent No.: US 7,674,437 B2
(45) Date of Patent: Mar. 9, 2010

(54) ANION GENERATING DEVICE UTILIZING SOLAR POWER

(76) Inventor: Chin-Kuang Luo, 5F, No. 56, Min-Chuan Rd., Chung Dist., Taichung City (TW)

( * ) Notice: Subject to any disclaimer, the term of this patent is extended or adjusted under 35 U.S.C. 154(b) by 993 days.

(21) Appl. No.: 11/408,092

(22) Filed: Apr. 20, 2006

(65) Prior Publication Data

US 2007/0039643 A1 Feb. 22, 2007

(30) Foreign Application Priority Data

Aug. 17, 2005 (TW) ............................. 94214079 U

(51) Int. Cl.
*B01J 19/08* (2006.01)
(52) U.S. Cl. ................... 422/186.04; 422/121
(58) Field of Classification Search ............ 422/186.04, 422/121
See application file for complete search history.

(56) References Cited

U.S. PATENT DOCUMENTS

| | | | | |
|---|---|---|---|---|
| 5,861,127 | A | * | 1/1999 | Yeh ............................. 422/121 |
| 6,843,964 | B2 | * | 1/2005 | Yeh ............................. 422/121 |
| 2005/0175512 | A1 | * | 8/2005 | Yuen ........................... 422/121 |

* cited by examiner

*Primary Examiner*—Kishor Mayekar
(74) *Attorney, Agent, or Firm*—Trop, Pruner & Hu, P.C.

(57) ABSTRACT

An anion generating device includes an outer housing formed with air inlet and outlets as well as a heat exchanging space, a fan unit disposed in the heat exchanging space, an anion generator operable so as to generate anions near a discharge electrode unit thereof disposed between the air outlet of the outer housing and an air outlet of the fan unit, and a power control unit disposed in a receiving space in the outer housing for supplying electrical power to each of the fan unit and the anion generator by means of electrical energy converted from solar power by a solar power collecting plate mounted on a heat conductive top wall of the outer housing. The anions are impelled by air expelled by the fan unit to move outwardly of the outer housing via the air outlet of the outer housing.

4 Claims, 2 Drawing Sheets

ANION GENERATING DEVICE UTILIZING SOLAR POWER

CROSS-REFERENCE TO RELATED APPLICATION

This application claims priority of Taiwanese Application No. 094214079, filed on Aug. 17, 2005.

BACKGROUND OF THE INVENTION

1. Field of the Invention

The invention relates to an anion generating device, more particularly to an anion generating device utilizing solar power.

2. Description of the Related Art

A conventional anion generating device typically utilizes an alternating current power or a battery set as a power source. The situation where the alternating current power is accidentally cut or the stored electrical power of the battery set is used up, leads to inconvenience during use.

SUMMARY OF THE INVENTION

Therefore, the object of the present invention is to provide an anion generating device that can utilize solar power.

According to the present invention, an anion generating device comprises:

an outer housing having a bottom wall, an inclined top wall made of a heat conductive material, and a surrounding wall interconnecting the top and bottom walls and cooperating with the top and bottom walls to define an accommodating space, the top wall having opposite lower and upper ends, the outer housing further having a partition disposed fixedly and inclinedly in the accommodating space and having a lower end connected to the bottom wall, and an upper end disposed adjacent to the upper end of the top wall and connected to the surrounding wall such that the accommodating space is divided into a heat exchanging space, and a receiving spaced is posed under the partition, the surrounding wall being formed with an air inlet disposed adjacent to the lower end of the top wall and in spatial communication with the heat exchanging space, and an air outlet adjacent to the upper end of the top wall and in spatial communication with the heat exchanging space;

a solar power collecting plate mounted on an outer surface of the top wall of the outer housing and adapted to convert solar power into electrical energy;

a fan unit disposed in the heat exchanging space and including a fan housing mounted on the partition and having an air inlet, and an air outlet disposed adjacent to the air outlet in the surrounding wall of the outer housing, and a fan disposed in the fan housing and operable so as to draw ambient air into the fan housing via the air inlet in the surrounding wall of the outer housing and the air inlet in the fan housing and so as to expel air in the fan housing via the air outlet in the fan housing toward the air outlet in the surrounding wall of the outer housing;

an anion generator including a generator body disposed in the receiving space in the outer housing, and a discharge electrode unit disposed in the heat exchanging space in the outer housing and between the air outlet in the fan housing and the air outlet in the surrounding wall of the outer housing, the anion generator being operable so as to generate a plurality of anions near the discharge electrode unit; and a power control unit disposed in the receiving space in the outer housing and connected electrically to the solar power collecting plate, the fan of the fan unit and the anion generator for supplying electrical power to each of the fan of the fan unit and the anion generator by means of electrical energy from the solar power collecting plate.

The anions generated by the anion generator are impelled by air expelled by the fan of the fan unit to move outwardly of the outer housing via the air outlet in the surrounding wall of the outer housing.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 1:
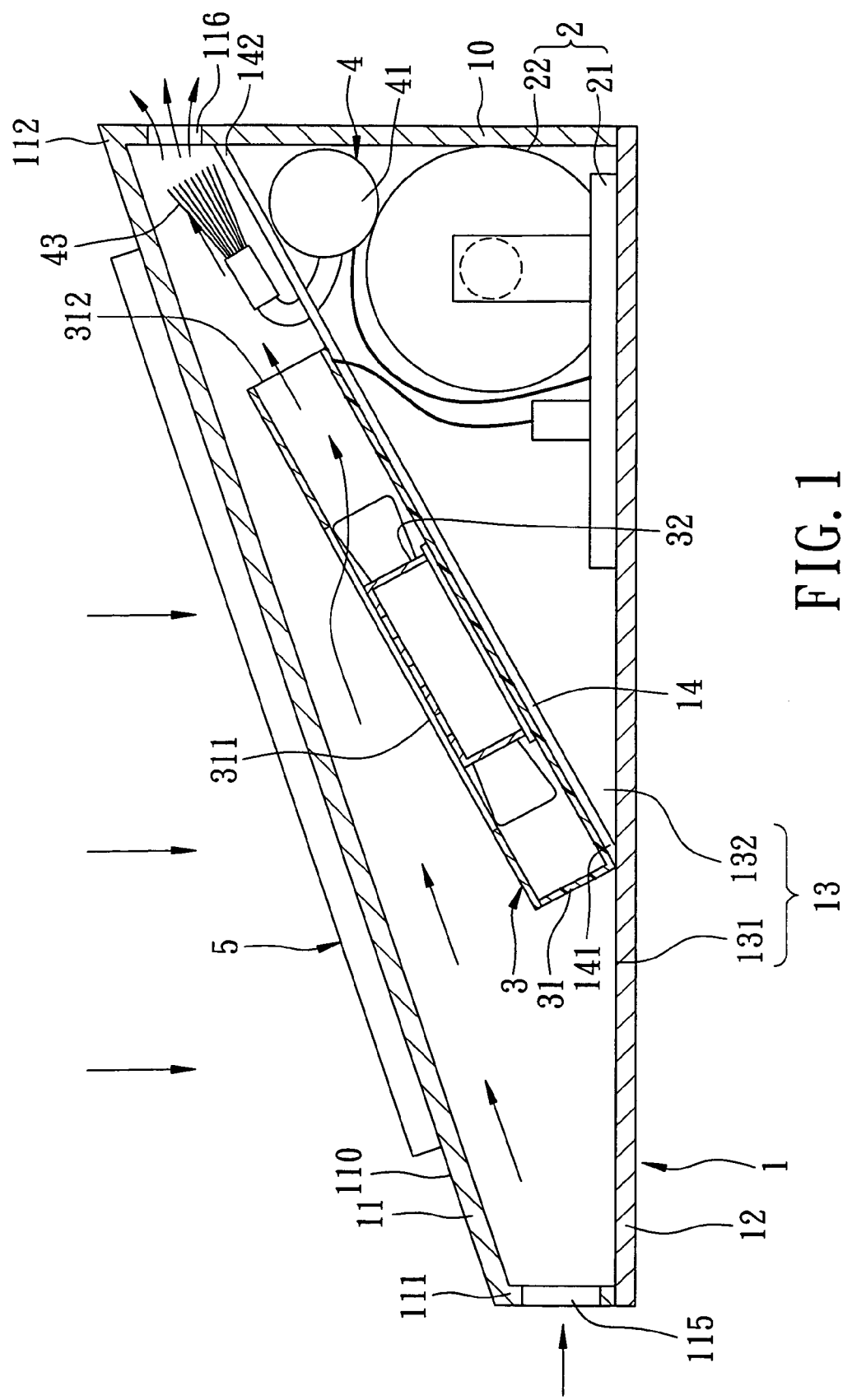
FIG. 1 is a partly sectional schematic view showing the preferred embodiment of an anion generating device according to the present invention.
Figure 2:
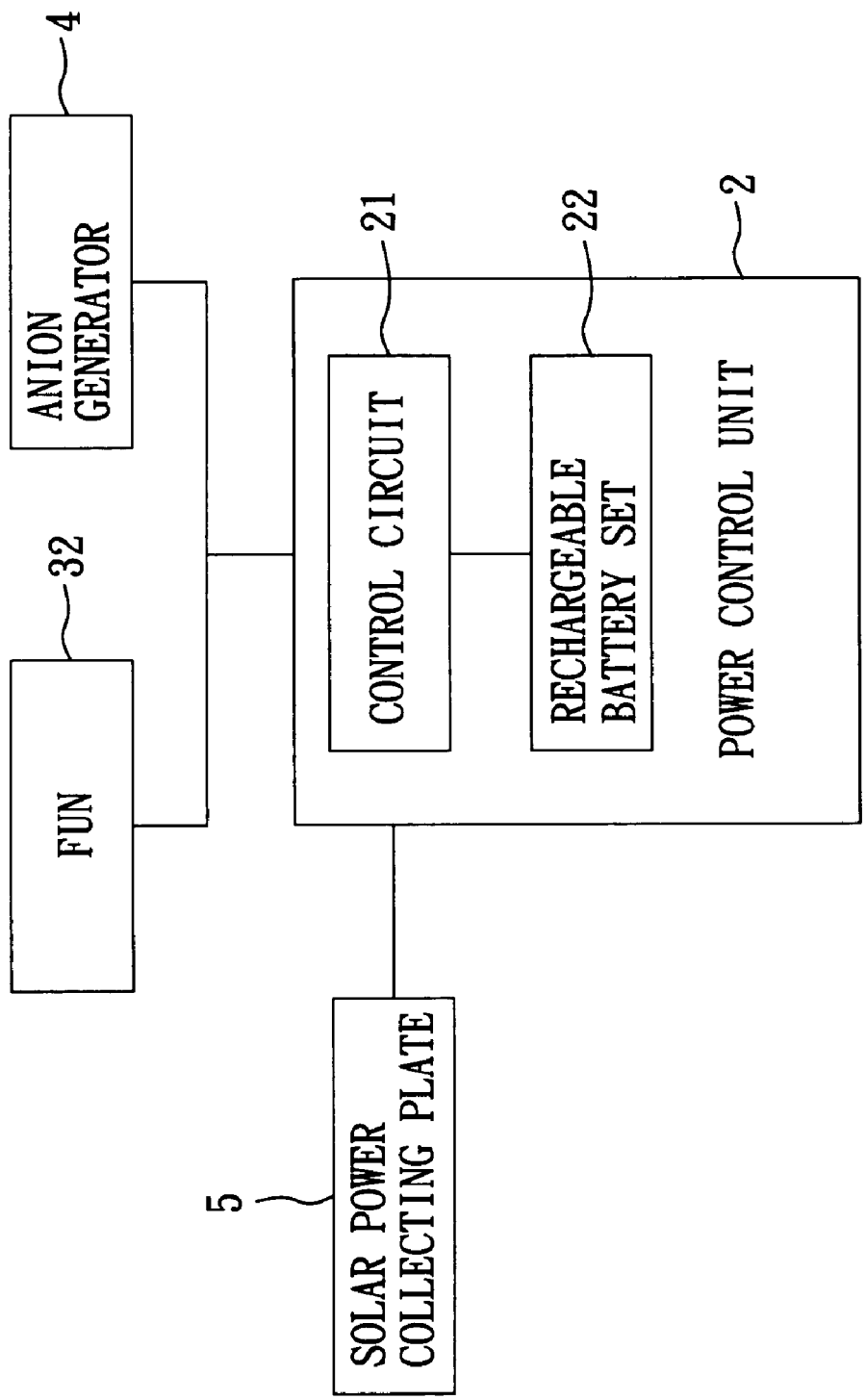
FIG. 2 is a schematic circuit block diagram illustrating the preferred embodiment.

Referring to FIGS. 1 and 2, the preferred embodiment of an anion generating device according to the present invention is shown to include an outer housing 1, a solar power collecting plate 5, a fan unit 3, an anion generator 4, and a power control unit 2.

The outer housing 1 has a bottom wall 12, an inclined top wall 11 made of a heat conductive material, and a surrounding wall 10 interconnecting the top and bottom walls 11, 12 and cooperating with the top and bottom walls 11, 12 to define an accommodating space 13. The top wall 11 has opposite lower and upper ends 111, 112. The outer housing 1 further has a partition 14 disposed fixedly and inclinedly in the accommodating space 13 and having a lower end 141 connected to the bottom wall 12, and an upper end 142 disposed adjacent to the upper end 112 of the top wall 11 and connected to the surrounding wall 10 such that the accommodating space 13 is divided into a heat exchanging space 131, and a receiving space 132 disposed under the partition 14. The surrounding wall 10 is formed with an air inlet 115 disposed adjacent to the lower end 111 of the top wall 11 and in spatial communication with the heat exchanging space 131, and an air outlet 116 adjacent to the upper end 112 of the top wall 11 and in spatial communication with the heat exchanging space 131. In this embodiment, the air outlet 116 in the surrounding wall 10 is smaller than the air inlet 115 in the surrounding wall 10.

The solar power collecting plate 5 is mounted on an outer surface 110 of the top wall 11 of the outer housing 1 and is adapted to covert solar power into electrical energy. In this embodiment, the outer surface 110 of the top wall 10 is inclined, thereby increasing solar power collecting efficiency by the solar power collecting plate 5.

The fan unit 3 is disposed in the heat exchanging space 131, and includes a fan housing 31 and a fan 32. The fan housing 31 is mounted on the partition 14, and has an air inlet 311, and an air outlet 312 disposed adjacent to the air outlet 116 in the surrounding wall 10 of the outer housing 1. In this embodiment, the fan unit 3 is a centrifugal fan. The air inlet 311 in the fan housing 31 extends in a direction perpendicular to that of the air outlet 312 in the fan housing 31. The fan 32 is disposed in the fan housing 31, and is operable so as to draw ambient air into the fan housing 31 via the air inlet 115 in the surrounding wall 10 of the outer housing 1 and the air inlet 311 in the fan housing 31 and so as to expel air in the fan housing 31 via the air outlet 312 in the fan housing 31 toward the air outlet 116 in the surrounding wall 10 of the outer housing 1.

The anion generator 4 includes a generator body 41 disposed in the receiving space 132 in the outer housing 1, and a discharge electrode unit 43 disposed in the heat exchanging space 131 in the outer housing 1 and between the air outlet 312 in the fan housing 31 and the air outlet 116 in the surrounding wall 10 of the outer housing 1. In this embodiment, the discharge electrode unit 43 of the anion generator 4 includes a plurality of needle electrodes. The anion generator 4 is operable so as to generate a plurality of anions near the discharge electrode unit 43.

The power control unit 2 is disposed in the receiving space 132 in the outer housing 1, and is connected electrically to the solar power collecting plate 5, the fan 32 of the fan unit 3 and the anion generator 4 for supplying electrical power to each of the fan 32 of the fan unit 3 and the anion generator 4 by means of the electrical energy from the solar power collecting plate 5. In this embodiment, the power control unit 2 includes a control circuit 21, and a rechargeable battery set 22 connected electrically to the control circuit 21. Under the control by the control circuit 21 in a known manner, the rechargeable battery set 22 is operated in one of a charging mode, where the electrical energy from the solar power collecting plate 5 is used to charge the rechargeable battery set 22, and a power supply mode, where the rechargeable battery set 22 supplies the electrical power to each of the fan 32 of the fan unit 3 and the anion generator 4.

As such, the anions generated by the anion generator 4 are impelled by air expelled by the fan 32 of the fan unit 3 to move outwardly of the outer housing 1 via the air outlet 116 in the surrounding wall 10 of the outer housing 1.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

I claim:

1. An anion generating device comprising:

an outer housing having a bottom wall, an inclined top wall made of a heat conductive material, and a surrounding wall interconnecting said top and bottom walls and cooperating with said top and bottom walls to define an accommodating space, said top wall having opposite lower and upper ends, said outer housing further having a partition disposed fixedly and inclinedly in said accommodating space and having a lower end connected to said bottom wall, and an upper end disposed adjacent to said upper end of said top wall and connected to said surrounding wall such that said accommodating space is divided into a heat exchanging space, and a receiving space disposed under said partition, said surrounding wall being formed with an air inlet disposed adjacent to said lower end of said top wall and in spatial communication with said heat exchanging space, and an air outlet adjacent to said upper end of said top wall and in spatial communication with said heat exchanging space;

a solar power collecting plate mounted on an outer surface of said top wall of said outer housing and adapted to convert solar power into electrical energy;

a fan unit disposed in said heat exchanging space and including
   a fan housing mounted on said partition and having an air inlet, and an air outlet disposed adjacent to said air outlet in said surrounding wall of said outer housing, and
   a fan disposed in said fan housing and operable so as to draw ambient air into said fan housing via said air inlet in said surrounding wall of said outer housing and said air inlet in said fan housing and so as to expel air in said fan housing via said air outlet in said fan housing toward said air outlet in said surrounding wall of said outer housing;

an anion generator including a generator body disposed in said receiving space in said outer housing, and a discharge electrode unit disposed in said heat exchanging space in said outer housing and between said air outlet in said fan housing and said air outlet in said surrounding wall of said outer housing, said anion generator being operable so as to generate a plurality of anions near said discharge electrode unit; and a power control unit disposed in said receiving space in said outer housing and connected electrically to said solar power collecting plate, said fan of said fan unit and said anion generator for supplying electrical power to each of said fan of said fan unit and said anion generator by means of electrical energy from said solar power collecting plate;

whereby, the anions generated by said anion generator are impelled by air expelled by said fan of said fan unit to move outwardly of said outer housing via said air outlet in said surrounding wall of said outer housing.

2. The anion generating device as claimed in claim 1, wherein said power control unit includes a rechargeable battery set.

3. The anion generating device as claimed in claim 1, wherein said fan unit is a centrifugal fan, said air inlet in said fan housing extending in a direction perpendicular to that of said air outlet in said fan housing.

4. The anion generating device as claimed in claim 1, wherein said air outlet in said surrounding wall of said outer housing is smaller than said air inlet in said surrounding wall of said outer housing.

* * * * *